United States Patent [19]

Ng

[11] Patent Number: 5,515,344
[45] Date of Patent: May 7, 1996

[54] MENSTRUAL CYCLE METER

[75] Inventor: Tai W. Ng, Hong Kong, Hong Kong

[73] Assignee: Wellgain Precision Products Ltd., Hong Kong

[21] Appl. No.: 269,200

[22] Filed: Jun. 30, 1994

[30] Foreign Application Priority Data

Jul. 1, 1993 [GB] United Kingdom .................. 9313618
Aug. 17, 1993 [GB] United Kingdom .................. 9317111

[51] Int. Cl.⁶ ........................ G04B 19/24; G04B 47/00; A61B 10/00
[52] U.S. Cl. ........................ 368/10; 368/28; 128/738; 364/413.01
[58] Field of Search ................. 368/10, 28–29, 368/82–84, 239–242; 128/738; 364/413.01, 413.02, 705, 715

[56] References Cited

U.S. PATENT DOCUMENTS 4,367,527  1/1983  Desjacques .
4,589,779  5/1986  Hatta et al. .................. 368/63
5,058,084  10/1991  Riesen ........................ 368/10

FOREIGN PATENT DOCUMENTS

WO88/06320  8/1988  WIPO .

*Primary Examiner*—Vit W. Miska
*Attorney, Agent, or Firm*—Gunn, Lee & Miller

[57] ABSTRACT

A menstrual cycle meter which comprises a casing microprocessor-based electronic circuitry including calendar keeping means and calculating means, a plurality of buttons provided on the casing to enable the microprocessor to receive user-input commands and/or data including the first day of at least the last two menstrual cycles of a user, and a display (12) provided on the casing and under the control of the microprocessor to display indication relating to the calculated fertile and infertile periods of the current menstrual cycle according to the stored input data. The display includes visual indicating means (58 & 59) for indicating the expected sex of a baby that is likely to be conceived in a particular day during the fertile period.

10 Claims, 4 Drawing Sheets

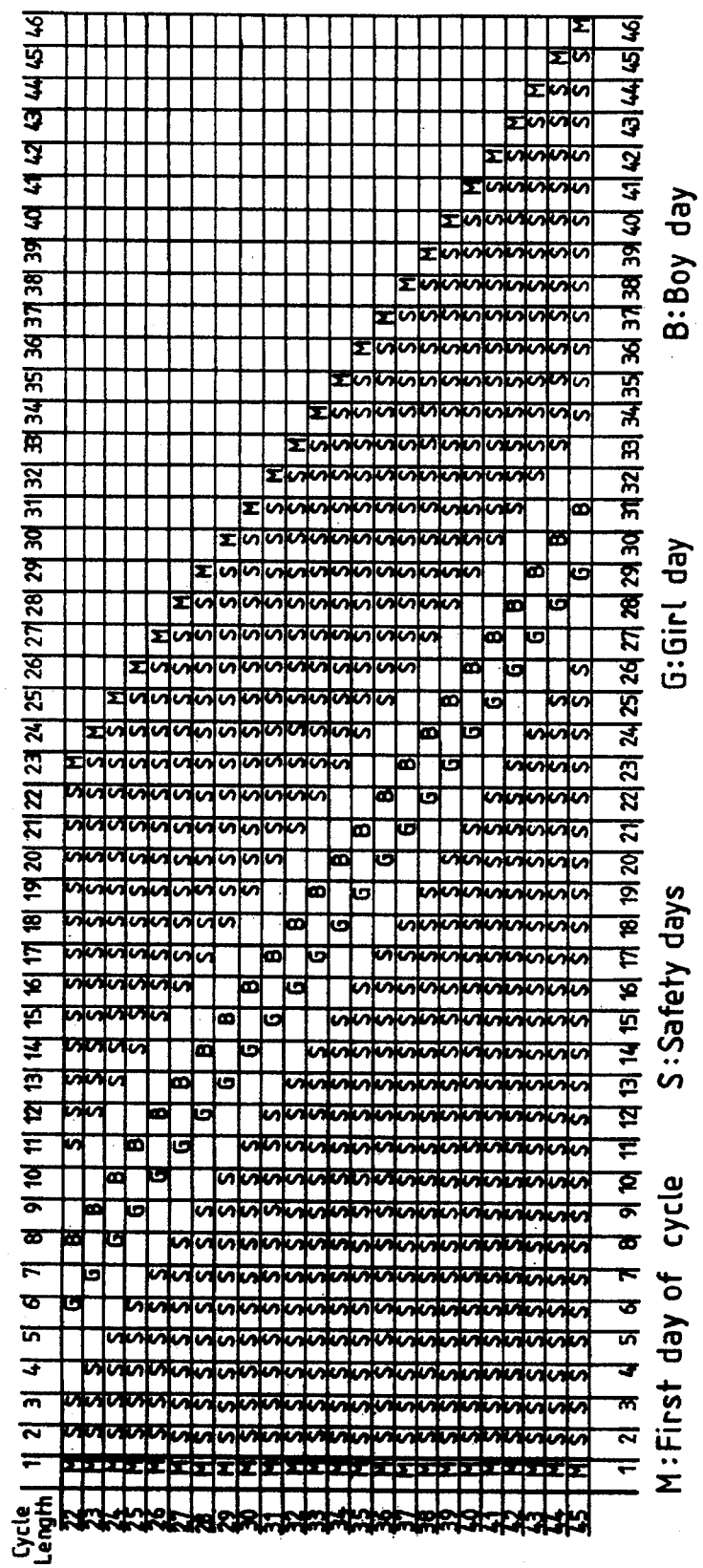
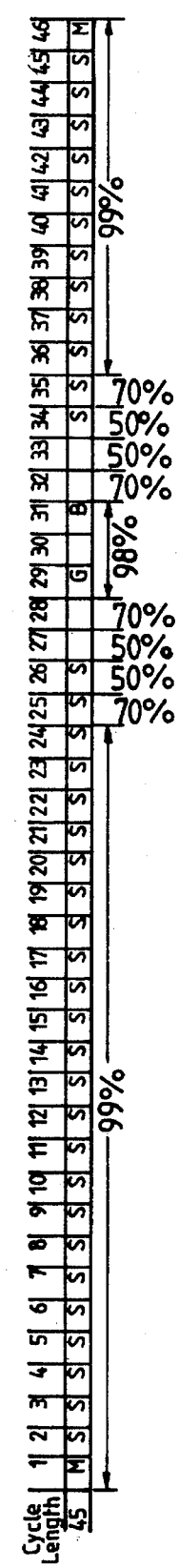
M: First day of cycle   S: Safety days   G: Girl day   B: Boy day
FIG. 3A
FIG. 3B

*CONNECT P30 & P31 FOR ENGLISH LANGUAGE

MENSTRUAL CYCLE METER

The present invention relates to a menstrual cycle meter.

SUMMARY OF THE INVENTION

According to the invention, there is provided a menstrual cycle meter which comprises a casing, microprocessor-based electronic circuitry including calendar keeping means and calculating means, a plurality of buttons provided on the casing to enable the microprocessor to receive user-input commands and/or data including the first day of at least the last two menstrual cycles of a user, and a display provided on the casing and under the control of the microprocessor to display indication relating to the calculated fertile and infertile periods of the current menstrual cycle according to the stored input data, said display including visual indicating means for indicating the expected sex of a baby that is likely to be conceived in a particular day during the fertile period.

Preferably, the visual indicating means is provided by graphical representations of a male and a female.

More preferably, the graphical representations are in the form of a male's head and a female's head.

In a preferred embodiment, the visual indicating means is arranged to have both the graphical representations appearing simultaneously in a particular day when the sex of the expected baby is uncertain.

Advantageously, the visual indicating means is arranged to flash on the day or days when the chance of successful conception is substantially high.

It is preferred that the microprocessor is programmed to determine the ovulation day as the fourteenth to sixteenth day before the calculated first day of the next menstrual cycle or to determine the range of possible ovulation day as from the fourteenth to sixteenth day before the calculated earliest possible first day of the next menstrual cycle to the fourteenth to sixteenth day before the calculated latest possible first day of the next menstrual cycle.

More preferably, the microprocessor is programmed to determine the fertile period as starting from about the fourth day before the or the earliest possible ovulation day to about the second day after the or the latest possible ovulation day.

In a preferred embodiment, the microprocessor is programmed to control the visual indicating means to indicate the sex of the expected baby being male from the or the latest possible ovulation day to about the second day after the or the latest possible ovulation day.

Preferably, the microprocessor is programmed to control the visual indicating means to indicate the sex of the expected baby being female from about the fourth day to about the second day before the or the earliest possible ovulation day.

It is preferred that the microprocessor is programmed to control the visual indicating means to indicate the sex of the expected baby being uncertain on about one day before the ovulation day or from about one day before the earliest possible ovulation day to about one day before the latest possible ovulation day.

The menstrual cycle meter may preferably further include audio alarm means under the control of the microprocessor to provide an audio alarm signal corresponding to the operation of the visual indicating means.

In a preferred embodiment, the display further includes additional visual indicating means for indicating the infertile period which is the period of the menstrual cycle excluding the fertile period.

The menstrual cycle meter may preferably further include personal access coding means for permitting use of the meter only by a user inputting the preset personal access code.

Advantageously, the electronic circuitry further includes timing means for the microprocessor to control the display to display real time.

Conveniently, the menstrual cycle meter further includes talking means under the control of the microprocessor to provide a simultaneous announcement of information corresponding to the information displayed on the display.

The invention will now be more particularly described, by way of example only, with reference to the accompanying drawings.

BRIEF DESCRIPTION OF THE DRAWINGS

FIG. 3A is an operation chart for the menstrual cycle meter of FIG. 1, and FIG. 3B shows the expected percentage of successful conception and safety level relating to the operation chart;

DETAILED DESCRIPTION OF PREFERRED EMBODIMENT(S)

Figure 1:
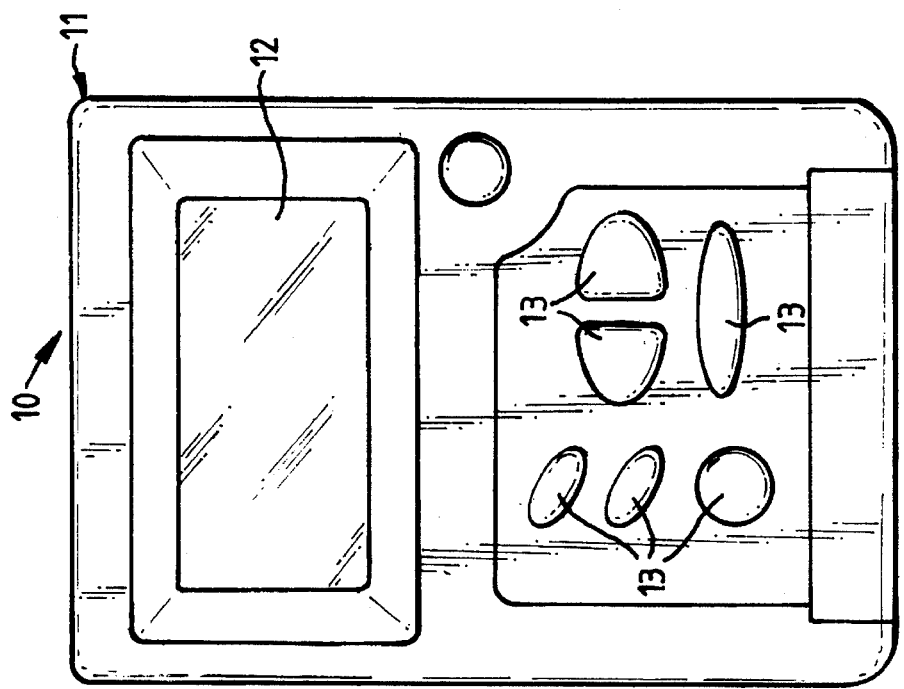
FIG. 1 is a front view of an embodiment of a menstrual cycle meter in accordance with the invention.
Figure 4:
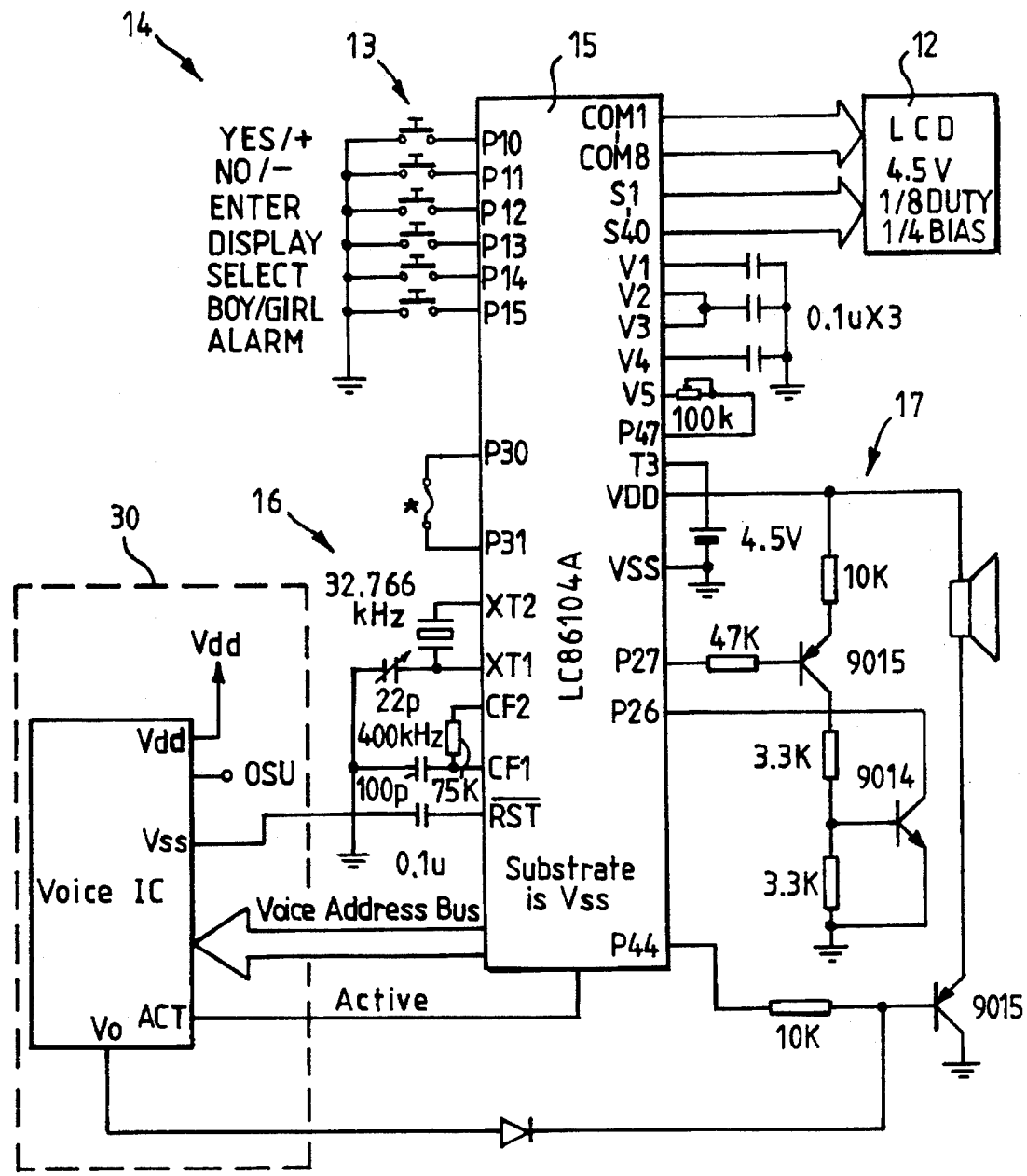
FIG. 4 is a schematic circuit diagram of microprocessor-based electronic circuitry of the menstrual cycle meter of FIG. 1.

Referring firstly to FIG. 1 of the drawings, there is shown a menstrual cycle meter 10 embodying the invention, which meter 10 comprises a casing 11 having thereon a LCD display 12 and a plurality of switch buttons 13 and containing therein microprocessor-based electronic circuitry 14 (FIG. 4).

Figure 2A:
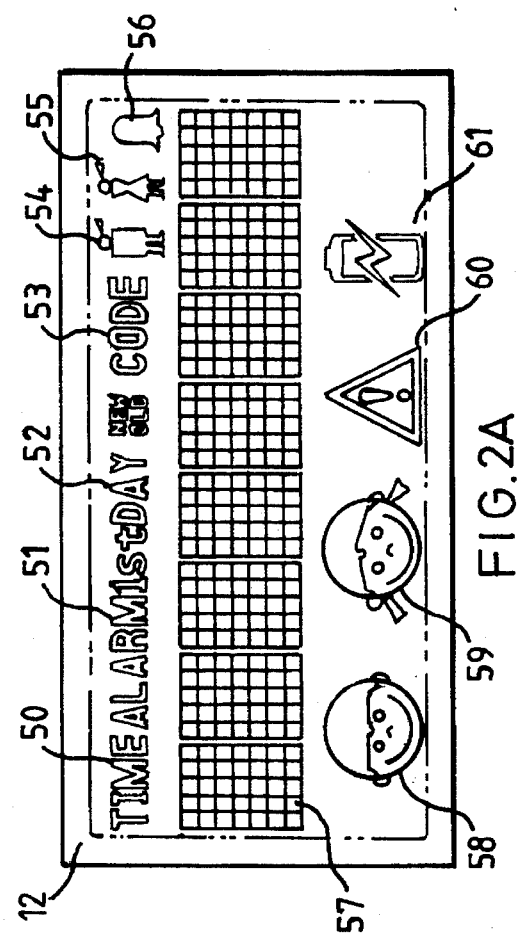
FIGS. 2A and 2B show two alternative display layouts of the menstrual cycle meter of FIG. 1.
Figure 2B:
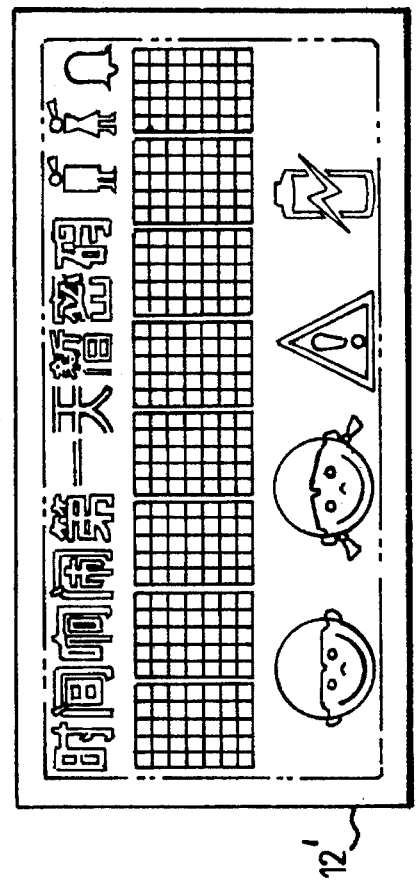

As shown in FIG. 2A, the display layout 12 is formed by three rows of display elements. The top row display elements are "TIME" 50, "ALARM" 51, "1st DAY" 52, "NEW/OLD CODE" 53, a boy's FIG. 54, a girl's FIG. 55 and a bell sign 56. The middle row display elements are provided by eight digits of 5×7 dot matrix 57 for displaying numeric data. The bottom row display elements consist of a boy's head 58, a girls's head 59, a triangular sign 60 and a low-battery sign 61. FIG. 2B shows an alternative display layout 12' having all equivalent text in Chinese characters. The switch buttons 13 include "YES/+", "NO/−", "ENTER", "DISPLAY", "SELECT" and "BOY/GIRL ALARM" (See FIG. 4).

As shown in FIG. 4, the electronic circuitry 14 is formed by a microprocessor 15 to which there are connected the LCD display 12 for various display purposes, the six aforenamed switch buttons 13 for data and/or command input by a user, a clock circuit 16 providing the necessary microprocessor running clock and the necessary basis for calendar and time keeping, and a speaker circuit 17 for providing various audio alarm signals.

The principal function of the microprocessor 15 is to receive and store the past history of menstruation of a female user and subsequently to predict the fertile and infertile periods of the next/forthcoming menstrual cycle based on the stored data and according to an algorithm corresponding to the operation chart shown in FIG. 3A.

In the operation chart, the horizontal coordinate represents the number of days and the vertical coordinate represents the menstrual cycle length in terms of days. The alphabets "M", "S", "G" AND "B" represent, in order, the first day of the menstrual cycle concerned, the safety (infertile) days, the Girl Day (as hereinafter defined) and the Boy Day (as hereinafter defined). The menstrual cycle length is the difference in days between two consecutive cycles. The operation chart caters for a range of menstrual cycle length between 22 and 45 days.

According to statistics, it has been observed that ovulation will most probably take place on about the 15th day (the 14th to 16th day) before the predicted first day of the next menstrual cycle. In the operation chart, the Boy Day is equivalent to the ovulation day and the Girl Day is about two days before the Boy Day. Observation also suggests that the fertile period normally starts from about the 4th day before to about the 2nd day after the ovulation day, outside which is the infertile or safety period of the menstrual cycle. Researches and evidences show that the sex of a baby likely to be conceived on or within about two days preceding the Girl Day will likely be female, and that the sex of a baby likely to be conceived on or within about two days following the Boy Day will likely be male. It is to be appreciated that an allowance of plus/minus one day should be given to the numbers of days mentioned above.

The microprocessor 15 is programmed according to the operation chart of FIG. 3A and based on the aforesaid observation and/or principle. Initially, the first dates of at least the last two menstrual cycles must be entered, for calculating the first day of the forthcoming menstrual cycle. Under the control of the microprocessor 15, the display 12 turns on the boy's head 58 or the girl's head 59 during the days when it is likely to conceive a baby boy or baby girl, respectively. Right on the Boy Day or the Girl Day, the appropriate head 58 or 59 will be flashing to emphasize a 98% chance of successful conception. On the day between the Boy Day and the Girl Day when it is uncertain to conceive whether a boy or a girl, the boy's and girl's heads 58 and 59 will both be turned on to indicate the uncertainty.

FIG. 3B shows the expected percentage of successful conception and safety level in each day of a menstrual cycle, taking a menstrual cycle length of 45 days as an example.

The internal memory of the microprocessor 15 is designed to count back 254 days or to process up to six menstrual cycle first days. If the menstrual cycle length of a user is or becomes less regular, the microprocessor 15 predicts for the next menstrual cycle both the longest possible and the shortest possible cycle length, thereby producing an earliest possible and a latest possible ovulation day. In this situation, the fertile period will be extended to lie between the 4th day prior to the earliest possible ovulation day and the 2nd day following the latest possible ovulation day, namely extended by the number of days of difference between the earliest and latest possible ovulation days. Conversely, the infertile/ safety period will be reduced by the same difference in days.

The period during which a baby girl is expected starts from the 4th day to the 2nd day before the earliest possible ovulation day, and that for expecting a baby boy covers the latest possible ovulation day and the two days immediately thereafter. This results in the uncertain days (uncertain as to the sex of the baby likely to be conceived) being extended from one day (in the case of regular menstrual cycle length) by the number of days of difference between the earliest and the latest possible ovulation days. In other words, the uncertain days will be from the day before the earliest possible ovulation day to the day before the latest possible ovulation day.

The menstrual cycle meter 10 is designed to determine the fertile period of the prevailing menstrual cycle, with an indication of the predicted sex of the baby likely to be conceived. Such information may equally well be useful to couples for taking appropriate contraceptive measures during the fertile period if babies are not wanted.

During the safety (infertile) period, the triangular sign 60 will be turned on. The low-battery sign 61 will appear when the battery for operating the electronic circuitry 14 becomes power deficient.

Figure 5:
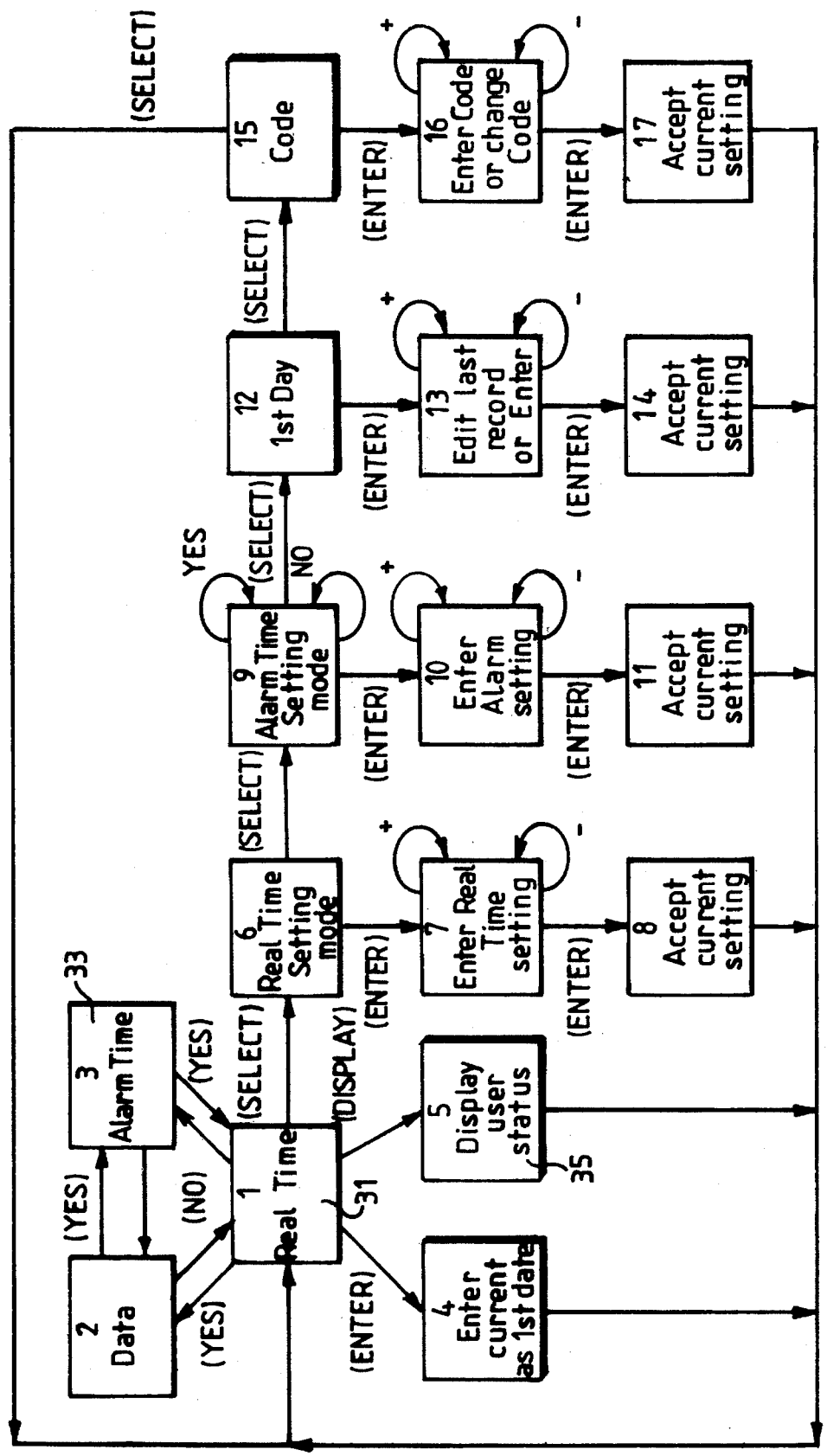
FIG. 5 is a flow chart illustrating the operation of the menstrual cycle meter of FIG. 1.

Referring to FIG. 5 of the drawings, the menstrual cycle meter 10 has five modes of operation, namely "Real Time", "Real Time Setting", "Alarm Time Setting", "1st Day" and "Code". The Real Time mode is the normal operation mode, displaying the real time on the dot matrix display 57. Pressing of the "YES/+" or "NO/–" button 13 will cycle the display 57 through the real time, the current date and the preset alarm time. Pressing of the "ENTER" button 13 will enter today's date as the first day of the forthcoming menstrual cycle. Pressing of the "DISPLAY" button 13 will bring up the user's menstruation or fertility status on the display 57, such as the expected percentage of successful conception on a fertile day and the expected birthday or the expected percentage of safety level on an infertile day and the expected first day of the next menstrual cycle.

The "Real Time Setting", "Alarm Time Setting", "1st Day" and "Code" modes are indicated by the "TIME" 50, "ALARM" 51, "1st DAY" 52 and "CODE" 53, respectively, on the display 12. These modes are selectable in turn by pressing of the "SELECT" button 13. In each of these modes, the "ENTER" button 13 is used to start entering and to finally accept input data, with the "YES/+" or "NO/–" button 13 used in the interim to increase or decrease by one the current input data displayed on the dot matrix display 57. The bell sign 56 will be turned on or off according to whether there is a time alarm set. In the "1st DAY" mode, when several menstrual cycle first days are to be entered, they must be entered one-by-one in repeated mode cycles and in consecutive chronological order.

The menstrual cycle meter 10 is provided with personal access coding so as to permit only one single current user using the meter 10, as the stored menstruation records are personal to that user. Any data inputting and/or changing must be preceded by the "CODE" mode for entering the preset access code first.

In addition to the visual indication provided by the boy's and/or girl's head 58 and 59, the menstrual cycle meter 10 also includes an audio boy/girl alarm which is to be set by means of the "BOY/GIRL ALARM" button 13. Either the boy or the girl alarm can be activated, but not both at the same time, and this is indicated by the boy's or girl's figure 54 or 55, respectively. Once a boy/girl alarm has been set, a two-second tone at each hour of the Boy or Girl Day will be given.

In a slightly modified version, the menstrual cycle meter 10 has an additional talking function which is provided by a voice integrated circuit or chip 30, as shown by dotted box in FIG. 4, through the operation of the speaker circuit 17. This talking function is particularly convenient to users who are weak or disabled in sight. The operation of the voice chip 30 is now described with reference to the flow chart of FIG. 5.

As described above, the "YES/+" or "NO/–" button 13 serves to cycle the dot matrix display 57 through displaying normally the real time (Box 31), the date (Box 32) and the alarm time (Box 33). With the voice chip 30 in place, both the date and the time will be announced when the date is displayed (Box 32), and the alarm time will be displayed as well as announced (Box 33). Also, pressing of the "DISPLAY" button 13 will cause the user's menstruation or fertility status to be displayed and simultaneously announced (Box 35).

The invention has been given by way of example only, and various modifications of and/or alterations to the described embodiment may be made by persons skilled in the art without departing from the scope of the invention as specified in the appended claims.

What is claimed is:

1. A menstrual cycle meter comprising a casing, microprocessor-based electronic circuitry including calendar keeping means and calculating means, a plurality of buttons provided on the casing to enable the microprocessor to receive user-input commands and/or data including the first day of at least the last two menstrual cycles of a user, and a display provided on the casing and under the control of the microprocessor to display indication relating to the calculated fertile and infertile periods of the current menstrual cycle according to the stored input data, said display including visual indicating means for indicating the expected sex of a baby that is likely to be conceived in a particular day during the fertile period wherein the microprocessor is programmed to determine the range of possible ovulation day as from the fourteenth to sixteenth day before the calculated earliest possible first day of the next menstrual cycle to the fourteenth to sixteenth day before the calculated latest possible first day of the next menstrual cycle.

2. A menstrual cycle meter as claimed in claim 1, wherein the microprocessor is programmed to determine the fertile period as starting from about tile fourth day before the earliest possible ovulation day to about the second day after the latest possible ovulation day.

3. A menstrual cycle meter as claimed in claim 1, wherein the microprocessor is programmed to control the visual indicating means to indicate the sex of the expected baby being male from the latest possible ovulation day to about the second day after the latest possible ovulation day.

4. A menstrual cycle meter as claimed in claim 1, wherein the microprocessor is programmed to control the visual indicating means to indicate the sex of the expected baby being female from about the fourth day to about the second day before the earliest possible ovulation day.

5. A menstrual cycle meter as claimed in claim 1, wherein the microprocessor is programmed to control the visual indicating means to indicate the sex of the expected baby being uncertain from about one day before the earliest possible ovulation day to about one day before the latest possible ovulation day.

6. A menstrual cycle meter as claimed in claim 1, further including audio alarm means under the control of the microprocessor to provide an audio alarm signal corresponding to the operation of the visual indicating means.

7. A menstrual cycle meter as claimed in claim 1, wherein the display further includes additional visual indicating means for indicating the infertile period which is the period of the menstrual cycle excluding the fertile period.

8. A menstrual cycle meter as claimed in claim 1, further including personal access coding means for permitting use of the meter only by a user inputting the preset personal access code.

9. A menstrual cycle meter as claimed in claim 1, wherein the electronic circuitry further includes timing means for the microprocessor to control the display to display real time.

10. A menstrual cycle meter as claimed in claim 1, further including talking means under the control of the microprocessor to provide a simultaneous announcement of information corresponding to the information displayed on the display.

* * * * *